(12) United States Patent
Ando et al.

(10) Patent No.: US 11,000,650 B2
(45) Date of Patent: May 11, 2021

(54) PROTECTOR AND MEDICAL NEEDLE ASSEMBLY

(71) Applicant: MEDIKIT CO., LTD., Tokyo (JP)

(72) Inventors: Hirokazu Ando, Tokyo (JP); Masahiro Umeda, Tokyo (JP)

(73) Assignee: MEDIKIT CO., LTD., Tokyo (JP)

( * ) Notice: Subject to any disclaimer, the term of this patent is extended or adjusted under 35 U.S.C. 154(b) by 0 days.

(21) Appl. No.: 16/478,922

(22) PCT Filed: Jun. 29, 2018

(86) PCT No.: PCT/JP2018/024801
§ 371 (c)(1),
(2) Date: Jul. 18, 2019

(87) PCT Pub. No.: WO2019/123698
PCT Pub. Date: Jun. 27, 2019

(65) Prior Publication Data
US 2020/0306460 A1  Oct. 1, 2020

(30) Foreign Application Priority Data

Dec. 19, 2017 (JP) .............................. JP2017-242265

(51) Int. Cl.
*A61M 5/32* (2006.01)
*A61M 5/34* (2006.01)

(52) U.S. Cl.
CPC ............ *A61M 5/3204* (2013.01); *A61M 5/34* (2013.01)

(58) Field of Classification Search
CPC ........ A61M 5/3204; A61M 5/34; A61M 5/32; A61M 5/3205; A61M 5/321; A61M 5/3213; A61M 2005/3215; A61M 5/3243; A61M 5/3245; A61M 5/3273; A61M 2005/3258; A61M 25/0612; A61M 25/0618; A61B 5/15176
See application file for complete search history.

(56) References Cited

U.S. PATENT DOCUMENTS 5,746,733 A * 5/1998 Capaccio ............. A61J 1/2096
141/329
2009/0270672 A1 * 10/2009 Fago ...................... G21F 5/018
600/5

FOREIGN PATENT DOCUMENTS

CN    203493994 U    3/2014
JP     91233/1986 U   6/1986
(Continued)

OTHER PUBLICATIONS

PCT/JP2018/024801, International Search Report dated Aug. 7, 2018.
(Continued)

*Primary Examiner* — Jason E Flick
(74) *Attorney, Agent, or Firm* — Meunier Carlin & Curfman LLC

(57) ABSTRACT

To provide a protector that is detachable with one hand and that eliminates the need of re-gripping a medical needle to perform puncture; and a medical needle assembly constituted by a combination of the protector and a medical needle.

A protector 1 is a protector that is detachably fitted and attached to a medical needle 2. When a proximal end portion of the protector 1 is pressed in a state in which the protector 1 is attached to the medical needle 2, the fitted state thereof is thereby released, and the protector 1 is detached from the medical needle 2.

10 Claims, 17 Drawing Sheets

(56) References Cited

FOREIGN PATENT DOCUMENTS

| | | |
|---|---|---|
| JP | S61-91233 U | 6/1986 |
| JP | 8-206195 A | 8/1996 |
| JP | H8-206195 A | 8/1996 |
| JP | 2000-84078 A | 3/2000 |
| JP | 2000084078 A | 3/2000 |
| JP | 2006-43327 A | 2/2006 |
| WO | 2005/079887 A1 | 9/2005 |

OTHER PUBLICATIONS

First Office Action issued for Japanese Patent Application No. 2017-242265, dated Feb. 9, 2020.
First Office Action issued for Chinese Patent Application No. 201880006627, dated Apr. 3, 2020.

* cited by examiner

FIG. 2
A
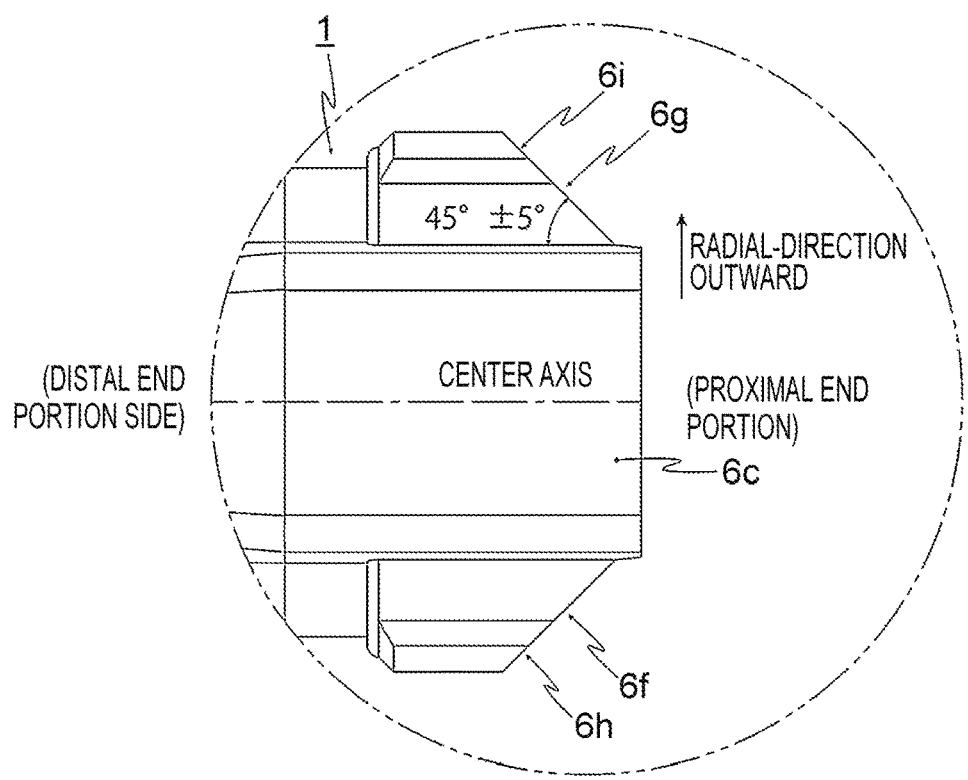
B
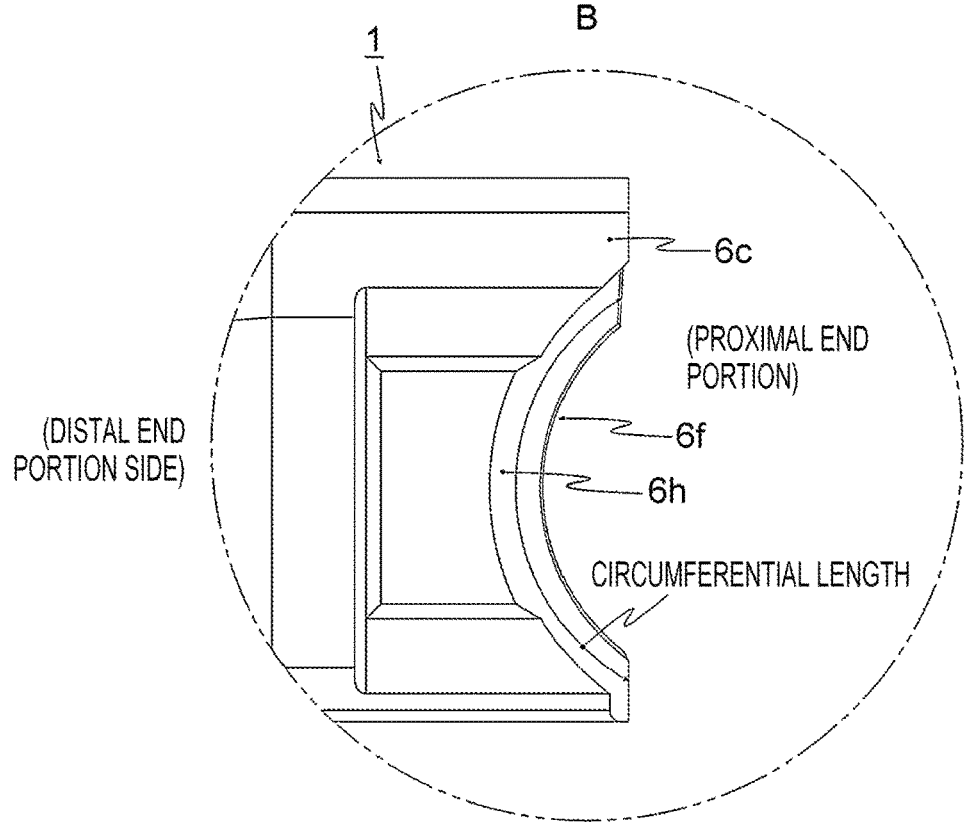

RIGHT-SIDE VIEW

FIG. 12
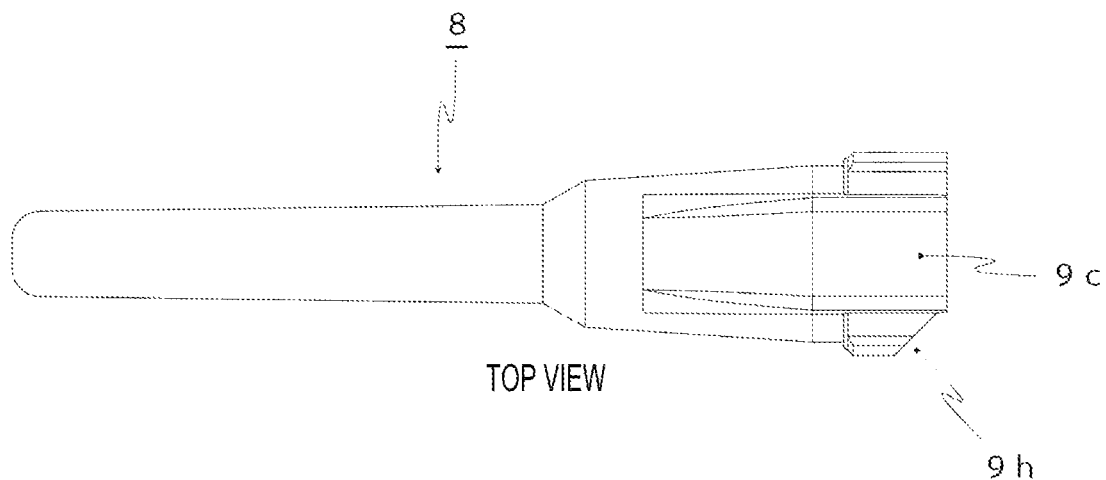
TOP VIEW
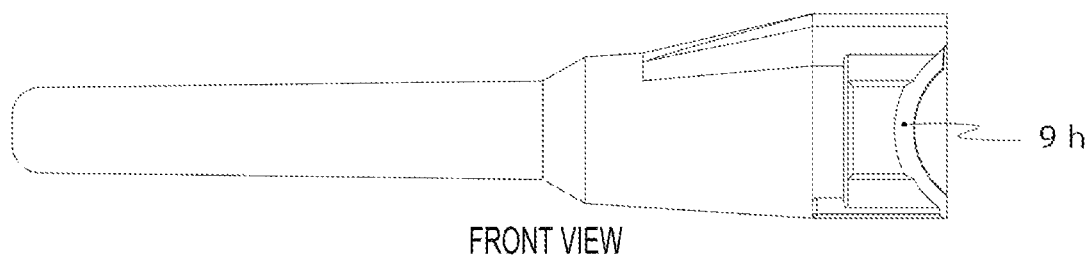
FRONT VIEW
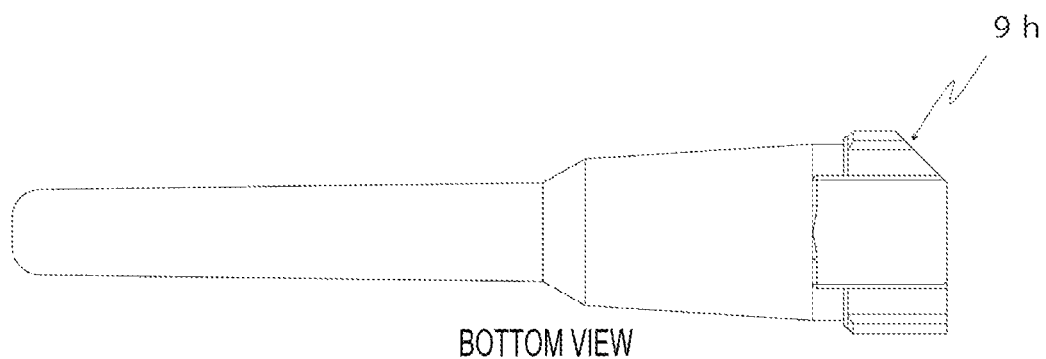
BOTTOM VIEW

PROTECTOR AND MEDICAL NEEDLE ASSEMBLY

CROSS-REFERENCE TO RELATED APPLICATIONS

This application is a national stage application filed under 35 U.S.C. § 371 of PCT/JP2018/024801 filed Jun. 29, 2018, which claims the benefit of and priority to Japanese Patent Application No. 2017-242265 filed Dec. 19, 2017, the disclosures of which are expressly incorporated herein by reference in their entirety.

TECHNICAL FIELD

The present invention relates to a protector and a medical needle assembly.

BACKGROUND ART

Medical needles include venous indwelling needles for use in fluid infusion (drip infusion) or the like, dialysis indwelling needles for use in dialysis, non-indwelling injection needles, and the like. Each of these medical needles constitutes a medical needle assembly by being attached with a protector (needle cap) that covers a needle tip to protect the needle body of a product before use.

If a protector that covers a needle tip is easily detachable, there is a concern that a medical worker may prick a finger or the like on the needle tip by accident. Therefore, each of a protector and a medical needle is generally provided with an engaging member. However, when employing a structure in which a protector is engaged with a medical needle, it is difficult to detach the protector with one hand because it is necessary to hold the medical needle with one hand and to grip and pull off the protector with the other hand to perform puncture.

Thus, a medical needle assembly such as that presented in PTL 1 has been proposed. The medical needle assembly disclosed in PTL 1 is capable of engaging a protector with a medical needle to suppress the protector from being easily detached during non-use such as during transport. The engaged state can be easily released for use to enable the protector to be detached with one hand.

The medical needle assembly (needle cap-attached syringe) disclosed in PTL 1 includes a needle (needle body), a needle-supporting member (hub), and a needle cap (protector), and the needle-supporting member and the needle cap are each provided with an engaging member and an inclined surface (refer to the claims in PTL 1).

For use, the thumb of a hand holding a syringe body is placed on a side surface of the needle cap in a state in which the needle cap is fitted to the needle-supporting member of the syringe body, and the needle cap is rotated in a direction of pressing the inclined surface of the needle cap against an inclined surface of a needle cap receiver. Consequently, a rotational force applied to the needle cap is converted into the force of pressing the needle cap in an axial direction due to an action of the inclined surface of the needle cap receiver. The needle cap is thereby moved forward relative to the syringe body, and the engaged state between a projection of the needle cap and a projection of the needle-supporting member is released. Accordingly, it is possible to easily detach the needle cap from the syringe body by a one-hand operation (refer to, for example, paragraph [0012] and FIG. 5 of PTL 1).

CITATION LIST

Patent Literature

PTL 1: Japanese Unexamined Patent Application Publication No. 2000-84077

SUMMARY OF INVENTION

Technical Problem

There is a case in which, before puncture with a venous indwelling needle or the like is performed, a target site is determined while a blood vessel is stretched and straightened with the left hand, disinfection is performed using the right hand, the venous indwelling needle or the like is then held, the blood vessel is stretched again, and the puncture is performed. In this case, a part in the vicinity of a distal end portion of a hub is gripped by the fingertips (finger pads) of the thumb and the index finger or the middle finger to perform the puncture.

However, in the configuration of the medical needle assembly disclosed in PTL 1, the needle cap (protector) is detached from the syringe body in a state in which the thumb of the hand holding the syringe body is placed on the side surface of the needle cap (protector). Thus, when the configuration in PTL 1 is applied to a venous indwelling needle or the like, there is a problem in which it is not possible to immediately enter a puncture stand-by state because re-gripping of the medical needle after detaching the protector is required to perform puncture.

Thus, it is an object of the present invention to provide a protector that is detachable with one hand and that eliminates the need of re-gripping a medical needle to perform puncture; and a medical needle assembly constituted by a combination of the protector and a medical needle.

Solution to Problem

To achieve the object, a configuration of the protector according to the present invention is characterized by (1) a protector to be detachably fitted and attached to a medical needle, the protector including an inclined surface provided at a proximal end portion of the protector so as to be externally exposed in a state in which the protector is attached to the medical needle, the inclined surface lowering in a direction opposite to a direction from the proximal end portion toward a distal end portion of the protector, in which when the inclined surface of the protector is pressed toward a center of the protector in a radial direction, the protector is moved forward, a fitted state thereof is thereby released, and the protector is detached from the medical needle.

The aforementioned configuration in (1) of the protector according to the present invention exerts the following effect. That is, in the aforementioned configuration in (1), the proximal end portion of the protector is gripped by the fingertips of the thumb and the index finger or the middle finger and pressed in this state toward the center of the protector in the radial direction (a one-touch operation). The force of pressing the proximal end portion of the protector is converted into the force of causing, via the inclined surface, the protector to move forward. Consequently, it is possible to detach the protector from the medical needle by causing the protector to move forward in the axial direction to release the fitted state between the protector and the medical needle.

In the state in which the protector is thus detached, the medical needle is in a state of being gripped by the fingertips of the thumb and the index finger or the middle finger. In other words, it is possible for the hand that has detached the protector to hold, without re-gripping, the medical needle. Thus, re-gripping of the medical needle is not required to perform puncture, and it is possible to immediately enter a puncture stand-by state. In other words, it is possible to perform puncture without changing a holding position. Thus, according to the aforementioned configuration in (1) of the protector according to the present invention, operability during a period between detaching of the protector and puncture is improved.

The following configurations in (2) and (3) are preferably applied to the aforementioned configuration in (1) of the protector according to the present invention.

(2) An inclined angle of the inclined surface relative to a center axis of the protector is in a range of 45°±10°. According to the aforementioned preferable configuration in (2), it is possible to efficiently convert the force of pressing the proximal end portion of the protector into the force of causing, via the inclined surface, the protector to move forward.

(3) The pressing part of the proximal end portion of the protector is notched. According to the aforementioned preferable configuration in (3), the fingertips of the thumb and the index finger or the middle finger are easily placed along the pressing part of the proximal end portion of the protector. Consequently, operability during detaching of the protector is improved. Moreover, it is possible to grip a portion closer to the distal end of the medical needle (portion closer by the axial-direction length of the notch to the distal end) by the fingertips of the thumb and the index finger or the middle finger in the state in which the protector is detached. Puncture is thus easily performed.

A configuration of the medical needle assembly according to the present invention is characterized by including (4) a medical needle that includes a needle body, a hub to which a proximal end portion of the needle body is fixed, and a fitting portion; and the protector described in any one of (1) to (3), the protector including a fitted portion to be fitted to the fitting portion and being detachably attached to the medical needle.

The aforementioned configuration in (4) of the medical needle assembly according to the present invention exerts the following effect. That is, according to the aforementioned configuration in (4), the proximal end portion of the protector is gripped by the fingertips of the thumb and the index finger or the middle finger and pressed in this state toward the center of the protector in the radial direction (a one-touch operation). The force of pressing the proximal end portion of the protector is converted into the force of causing, via the inclined surface, the protector to move forward. Consequently, it is possible to detach the protector from the medical needle by causing the protector to move forward in the axial direction to release the fitted state between the protector and the medical needle.

In the state in which the protector is thus detached, the medical needle is in a state of being gripped by the fingertips of the thumb and the index finger or the middle finger. In other words, it is possible for the hand that has detached the protector to hold, without re-gripping, the medical needle. Thus, re-gripping of the medical needle is not required to perform puncture, and it is possible to immediately enter the puncture stand-by state. In other words, it is possible to perform puncture without changing a holding position. Thus, according to the aforementioned configuration in (4) of the medical needle assembly according to the present invention, operability during the period between detaching of the protector and puncture is improved.

The following configuration in (5) is preferably applied to the aforementioned configuration in (4) of the medical needle assembly according to the present invention.

(5) The pressing part of the proximal end portion of the protector is positioned in the vicinity of the distal end portion of the hub in a state in which the protector is attached to the medical needle. According to the aforementioned preferable configuration in (5), it is possible to grip a part in the vicinity of the distal end portion of the hub of the medical needle by the fingertips of the thumb and the index finger or the middle finger in the state in which the protector is detached. Moreover, it is possible to reduce the effect of hand shake by holding a part closer to the needle tip when gripping the hub of the medical needle, thereby improving precision in puncture of a target site.

Advantageous Effects of Invention

According to the present invention, it is possible to detach a protector with one hand and perform puncture immediately without the need of re-gripping a medical needle to perform the puncture.

BRIEF DESCRIPTION OF DRAWINGS

FIG. 2 is an enlarged view of circular portions A and B indicated by the long dashed double-short dashed lines in FIG. 1.

FIG. 12 is a top view, a front view, and a bottom view illustrating another configuration of the protector according to the present invention.

DESCRIPTION OF EMBODIMENTS

Hereinafter, the present invention will be specifically described by using suitable embodiments. Note that the embodiments described below are merely examples in which the present invention is embodied, and the present invention is not limited to the embodiments.

First Embodiment (Configurations of Protector and Medical Needle Assembly)

The configurations of a protector and a medical needle assembly according to a first embodiment of the present invention will be described with reference to FIGS. 1 to 7 by presenting an example in which the medical needle is a venous indwelling needle.

Figure 3:
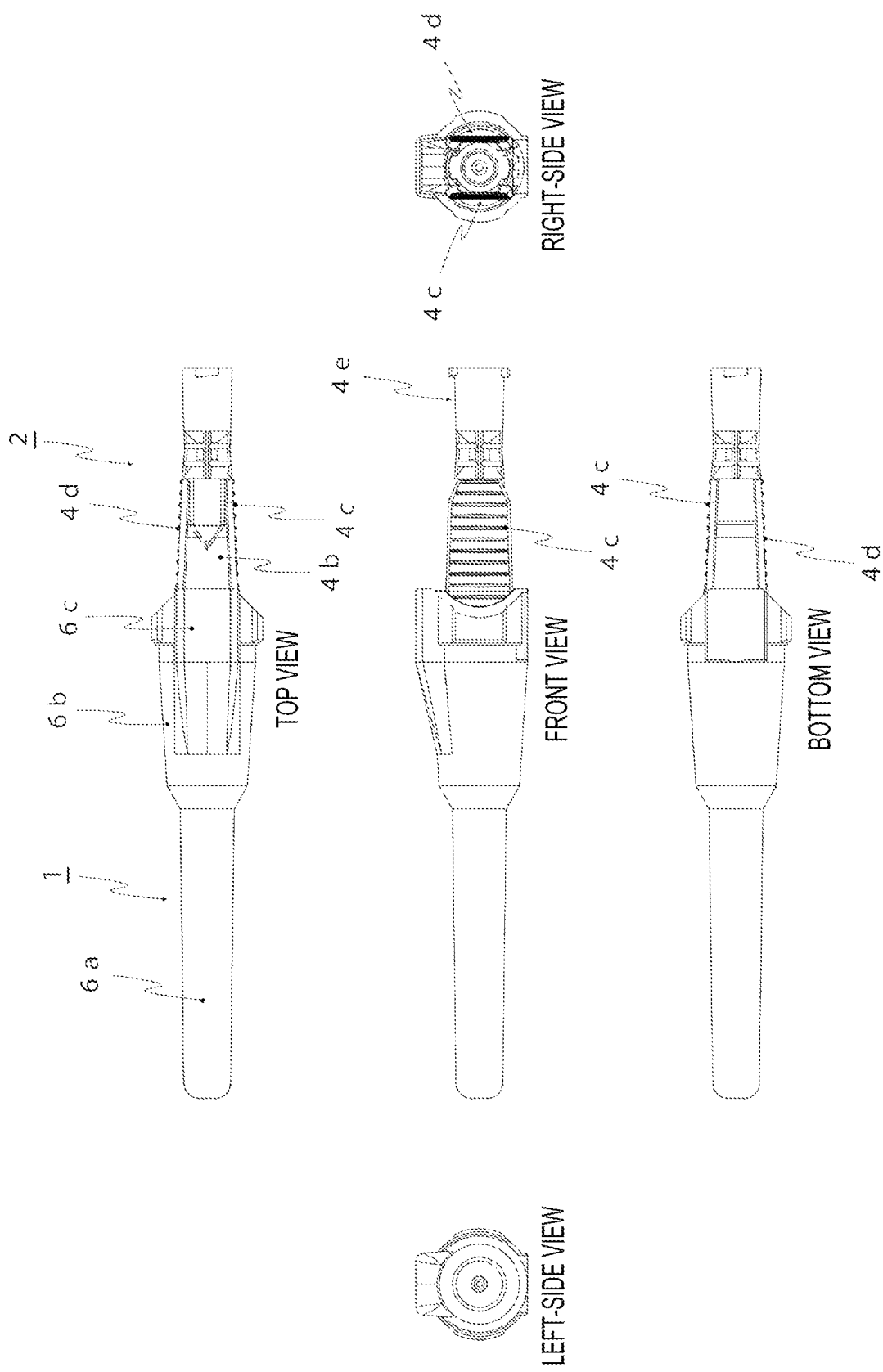
FIG. 3 is a six-view drawing (the rear view, which appears symmetrically with the front view, is omitted) illustrating a configuration of a medical needle assembly according to the first embodiment of the present invention.
Figure 5:
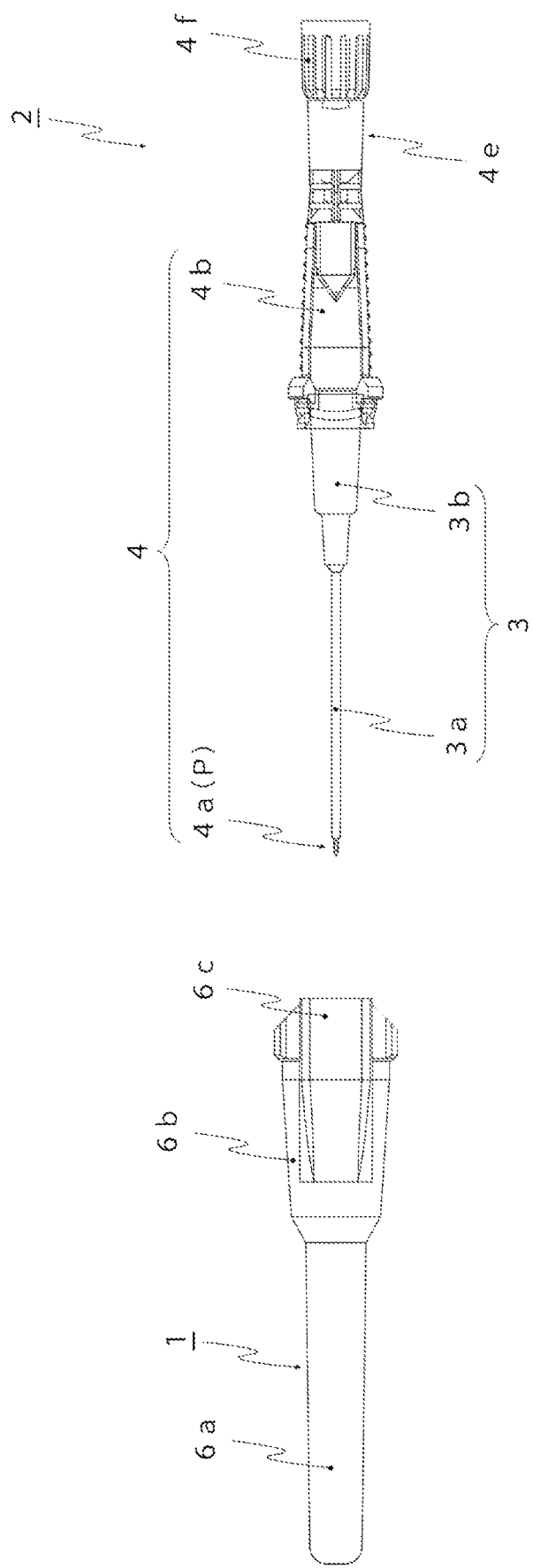
FIG. 5 is an exploded plan view illustrating the configuration of the medical needle assembly according to the first embodiment of the present invention.
Figure 10:
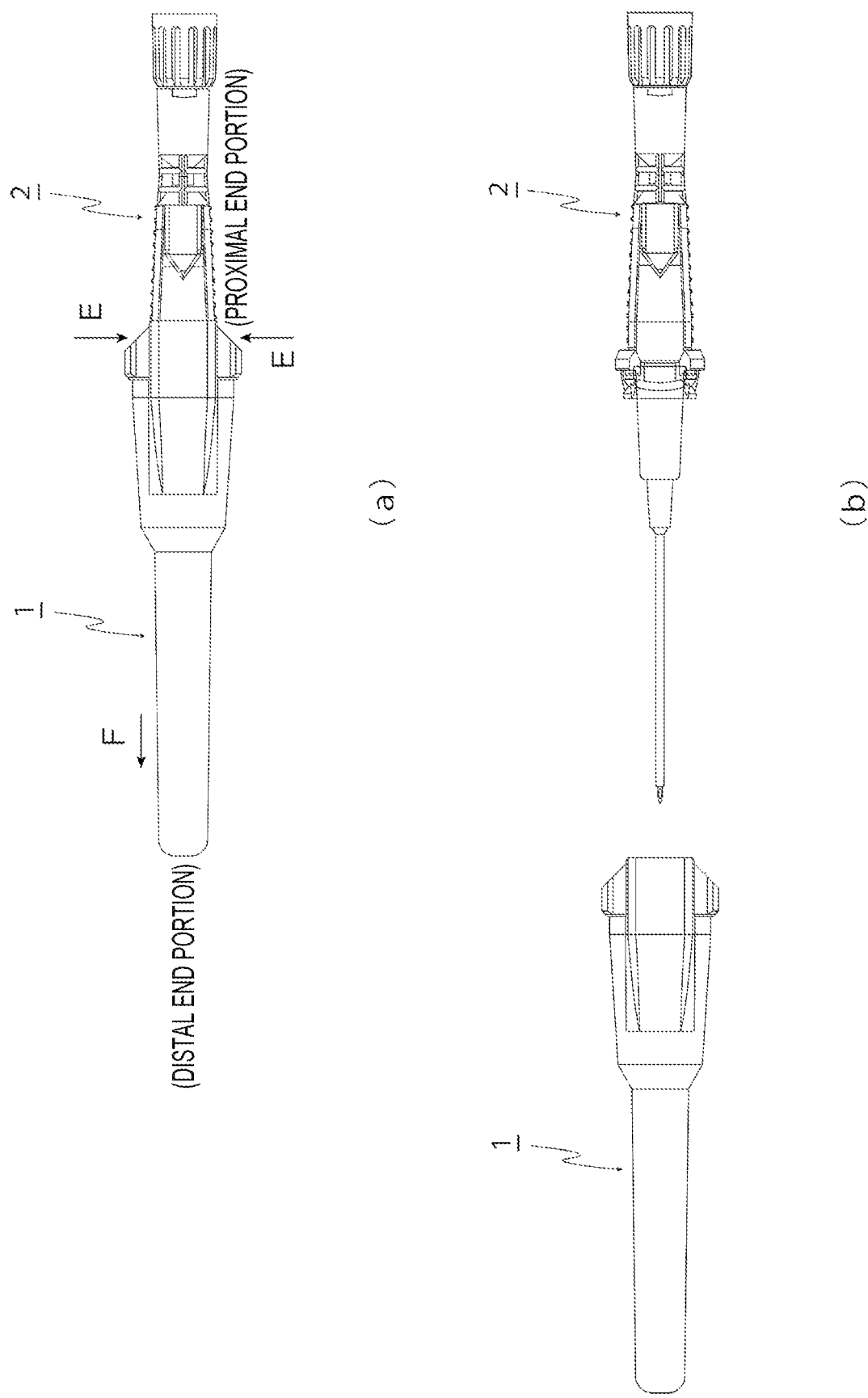
FIG. 10 is a plan view illustrating the use method of the medical needle assembly according to the first embodiment of the present invention.
Figure 11:
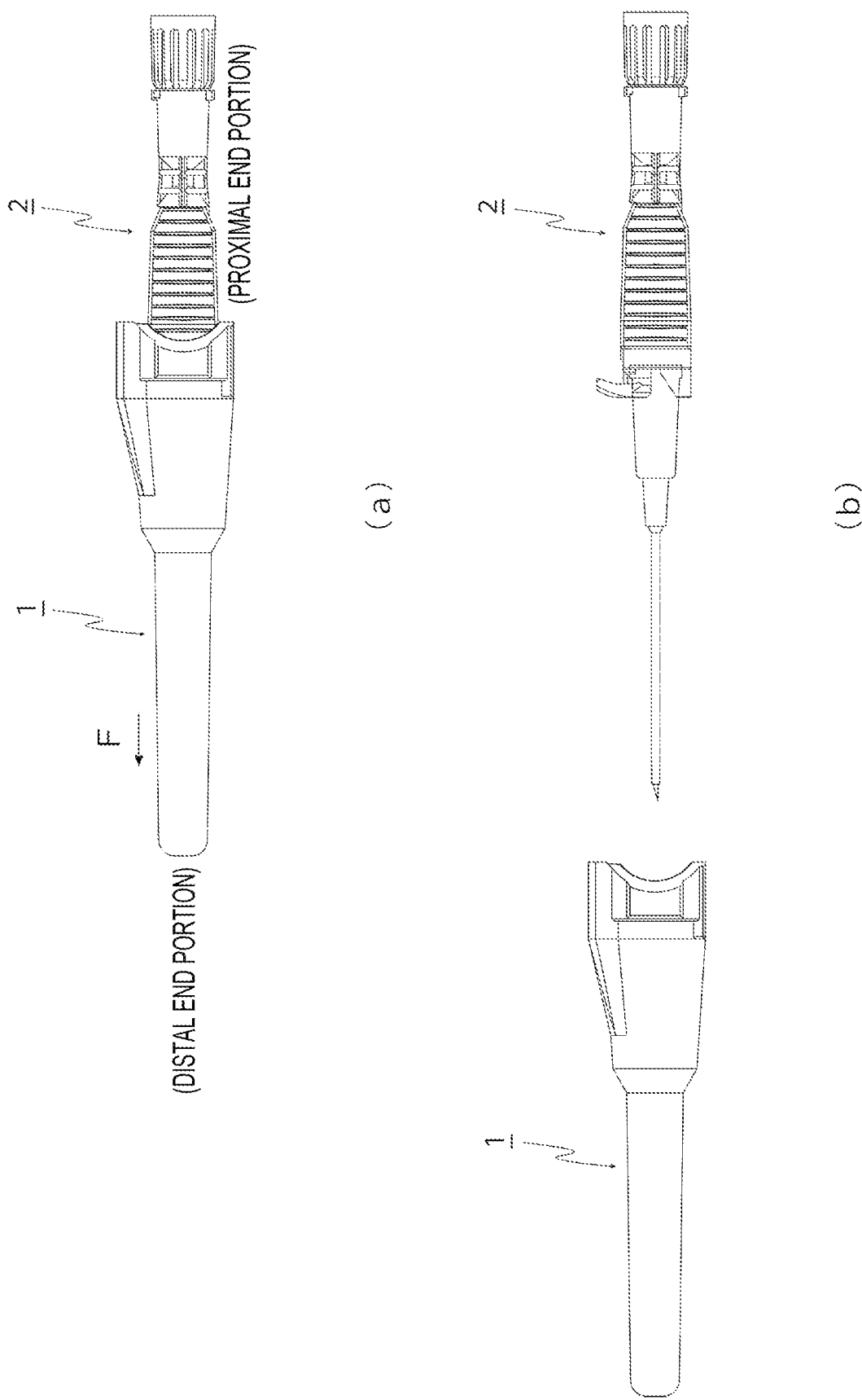
FIG. 11 is a front view illustrating the use method of the medical needle assembly according to the first embodiment of the present invention.

The medical needle assembly illustrated in FIG. 3 and FIG. 5 includes a medical needle 2 and a protector 1. The protector 1 is detachably fitted and attached to the medical needle 2. When a proximal end portion of the protector 1 is pressed toward (arrow E direction) the center of the protector 1 in the radial direction in a state in which the protector 1 is attached to the medical needle 2 as illustrated in FIG. 10(a) and FIG. 11(a), the protector 1 is moved forward in the axial direction (arrow F direction). The fitted state is thereby released, and the protector 1 is detached from the medical needle 2 as illustrated in FIG. 10(b) and FIG. 11(b).

Hereinafter, more specific description will be provided. The medical needle 2 illustrated in FIG. 3 and FIG. 5 is a venous indwelling needle and includes an outer needle 3 and an inner needle 4. The outer needle 3 includes a catheter 3a and a catheter hub 3b. The catheter 3a is formed by a thin flexible tube made of polyurethane. The catheter hub 3b is a hard cylinder-like member made of polycarbonate and is integral with a proximal end portion of the catheter 3a. The inner needle 4 includes a metal inner needle 4a (needle body) and a hub 4b. The metal inner needle 4a is made of stainless steel, has a diameter that is insertable through the catheter 3a substantially with no gap, and has a puncture blade at a needle tip P. The hub 4b is a hard cylinder-like member made of polycarbonate and is fixed to a proximal end portion of the metal inner needle 4a. In a state in which the metal inner needle 4a is inserted through the catheter 3a, the proximal end of the catheter hub 3b is attached to the distal end of the hub 4b.

Figure 4:
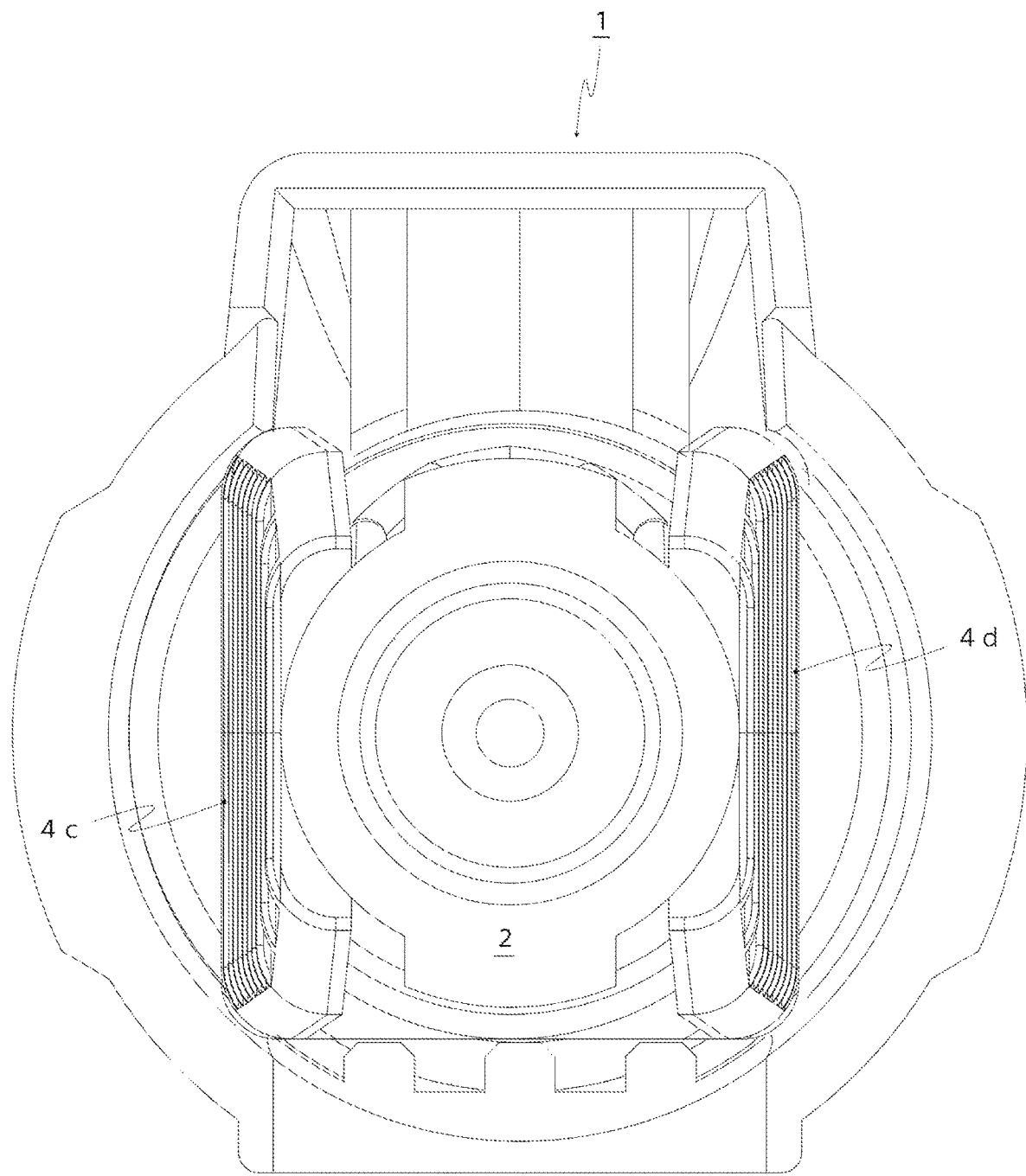
FIG. 4 is an enlarged view of the right-side view in FIG. 3.

The outer needle 3 includes an astriction supporting valve (not illustrated) incorporated therein and is capable of supporting astriction when the inner needle is extracted after puncture. As illustrated in FIG. 3 and FIG. 4, the hub 4b includes anti-slip ribs 4c and 4d formed on the front side and the rear side, respectively, and enables the medical needle 2 to be tightly held when puncture is performed.

As illustrated in FIG. 3 and FIG. 5, a backflow-blood confirmation portion 4e is provided at the rear end of the hub 4b. A target site is punctured in a state in which the metal inner needle 4a is inserted through the catheter 3a as illustrated in FIG. 5, the hub 4b is gripped by the fingertips of the thumb and the index finger or the middle finger after backflow blood is confirmed through the backflow-blood confirmation portion 4e, and only the inner needle 4 is extracted.

As illustrated in FIG. 5, an air plug 4f is detachably provided at the rear end of the backflow-blood confirmation portion 4e. The air inside the hub 4b is discharged through the air plug 4f during confirmation of backflow blood; however, blood is not allowed to pass through the air plug 4f and thus does not leak to the outside.

Figure 1:
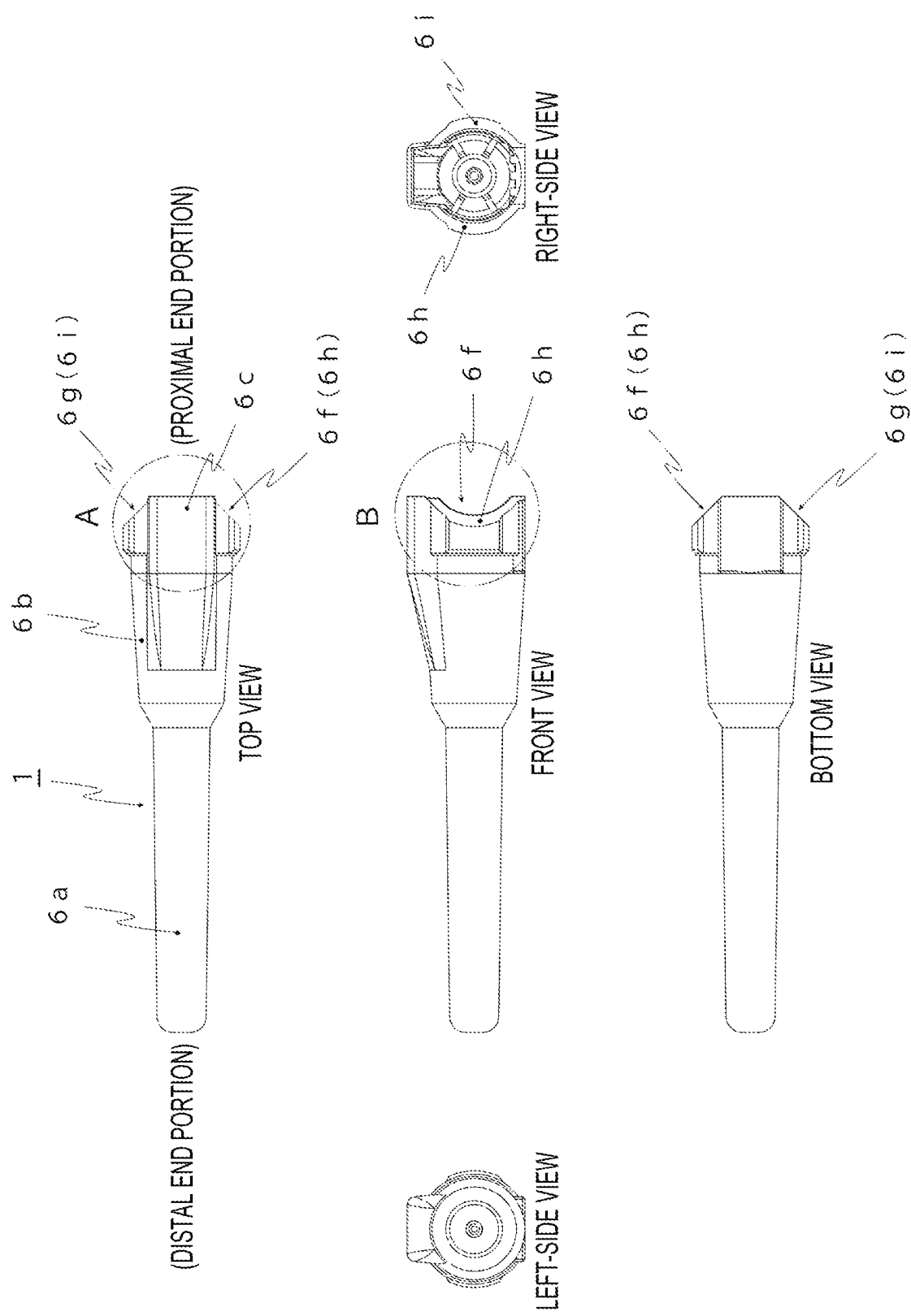
FIG. 1 is a six-view drawing (the rear view, which appears symmetrically with the front view, is omitted) illustrating a configuration of a protector according to a first embodiment of the present invention.

The protector 1 is made of polypropylene and includes a first protector body portion 6a, a second protector body portion 6b, and a proximal end portion 6c, as illustrated in FIG. 1, FIG. 3, and FIG. 5. The first protector body portion 6a covers the catheter 3a through which the metal inner needle 4a is inserted. The second protector body portion 6b covers the catheter hub 3b. The proximal end portion 6c covers a distal end portion of the hub 4b of the medical needle 2.

Figure 6:
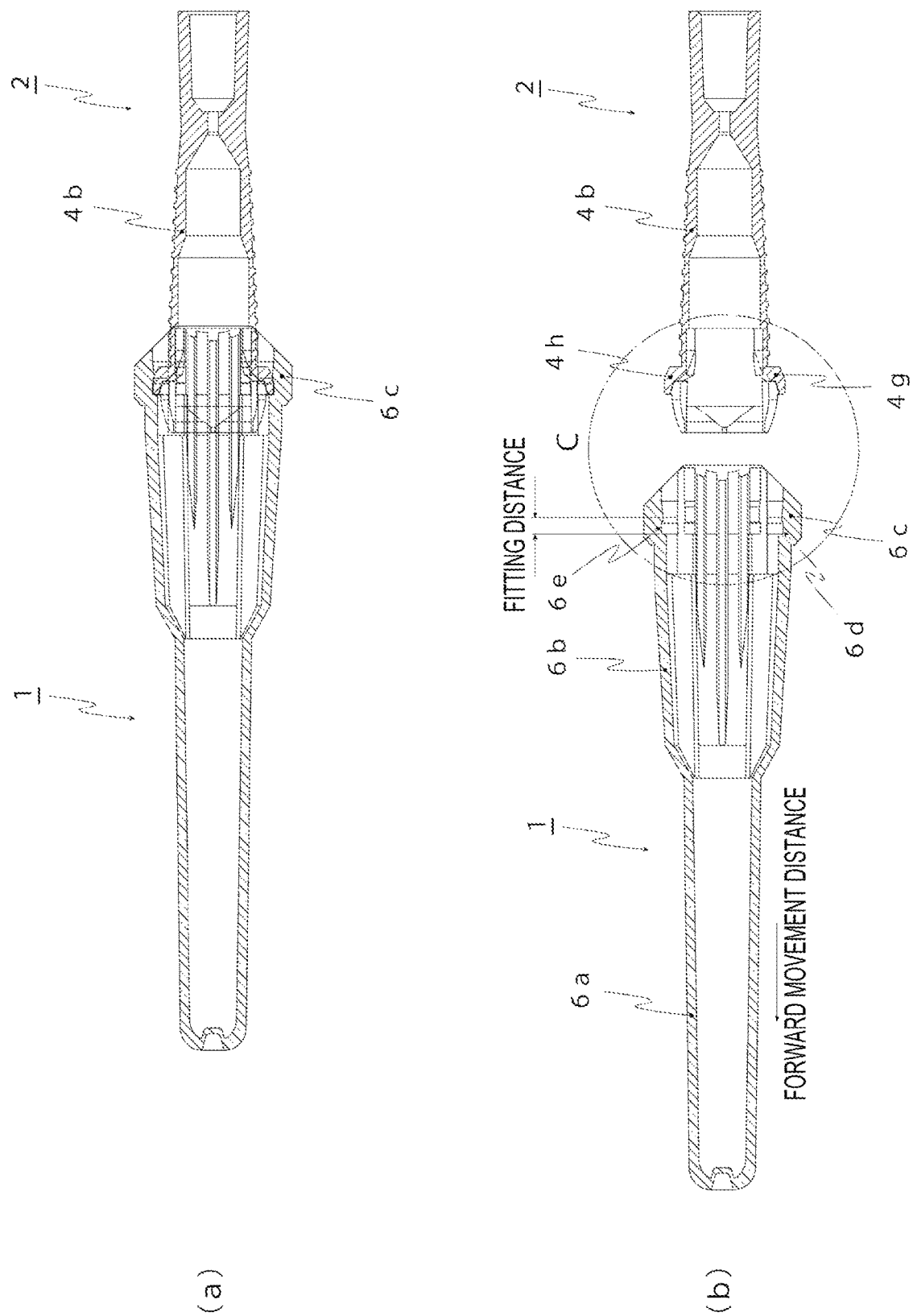
FIG. 6 is a sectional plan view (a needle body, an outer needle, and an air plug are omitted) for describing a medical needle-protector fitting mechanism of the medical needle assembly according to the first embodiment of the present invention.
Figure 7:
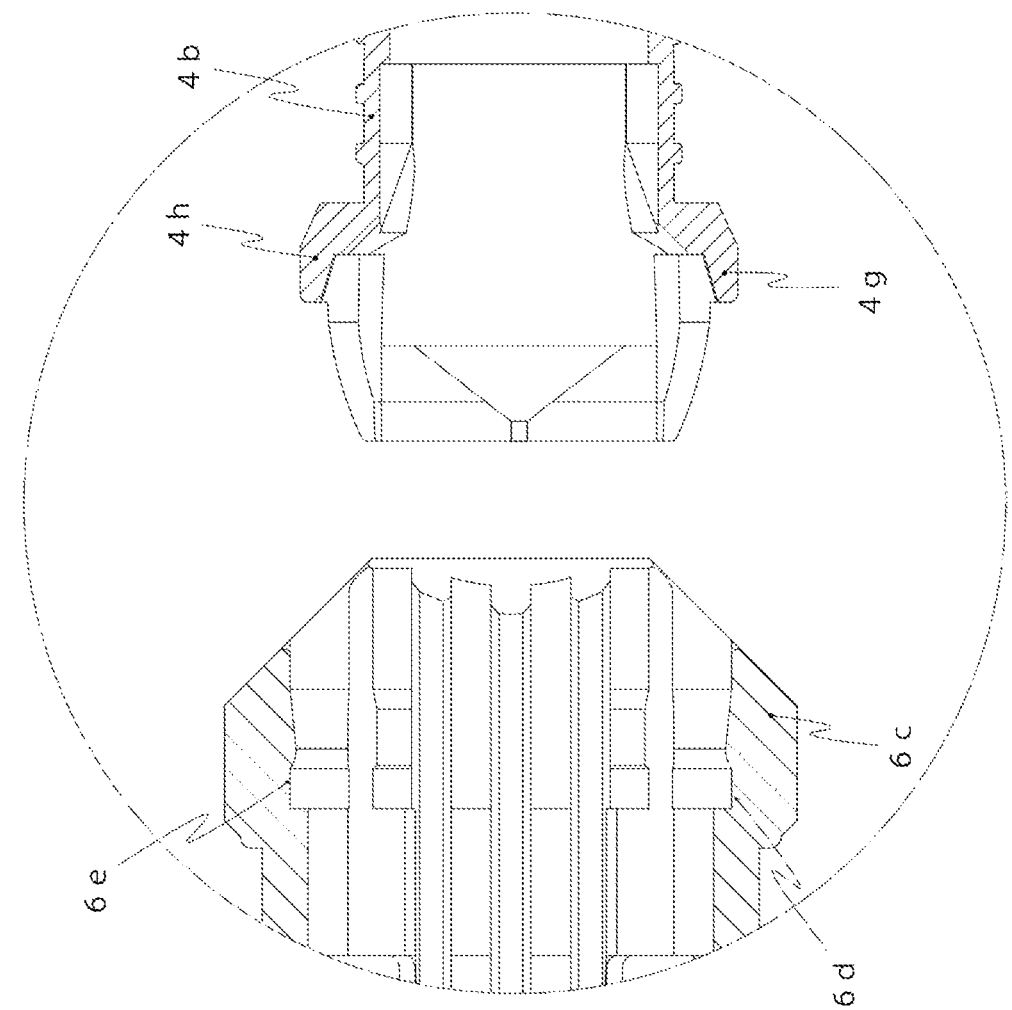
FIG. 7 is an enlarged view of circular portion C indicated by the long dashed double-short dashed line in FIG. 6.

As illustrated in FIG. 6 and FIG. 7, fitting portions 4g and 4h each having a projecting shape are formed on the front side and the rear side of an outer circumferential surface of the distal end portion of the hub 4b of the medical needle 2. Fitted portions 6d and 6e that are respectively fitted to the fitting portions 4g and 4h are formed on the front side and the rear side of an inner circumferential surface of the proximal end portion 6c of the protector 1. The fitted portions 6d and 6e each have a recessed shape substantially identical to the shape of the distal end of each of the fitting portions 4g and 4h, and, when the protector 1 is attached to the medical needle 2, the fitting portions 4g and 4h are fitted into the fitted portions 6d and 6e, and both portions enter a fitted state.

As illustrated in FIG. 1 and FIG. 2, arc-shaped notches 6f and 6g are formed on the front side and the rear side of the proximal end portion 6c of the protector 1. In addition, inclined surfaces 6h and 6i lowering in a direction opposite to a direction from the proximal end portion 6c toward the distal end portion of the protector 1 are formed at the edges of the notches 6f and 6g.

In other words, the inclined surfaces 6h and 6i are inclined surfaces inclining outward in the radial direction of the protector 1 from the proximal end portion 6c toward the distal end portion of the protector 1. In other words, the inclined surfaces 6h and 6i are inclined surfaces inclining such that pressing parts become thicker from the proximal end portion 6c toward the distal end portion of the protector 1. In other words, the inclined surfaces 6h and 6i are inclined surfaces inclining such that the circumferential length of each of the pressing parts increases from the proximal end portion 6c toward the distal end portion of the protector 1.

Figure 8:
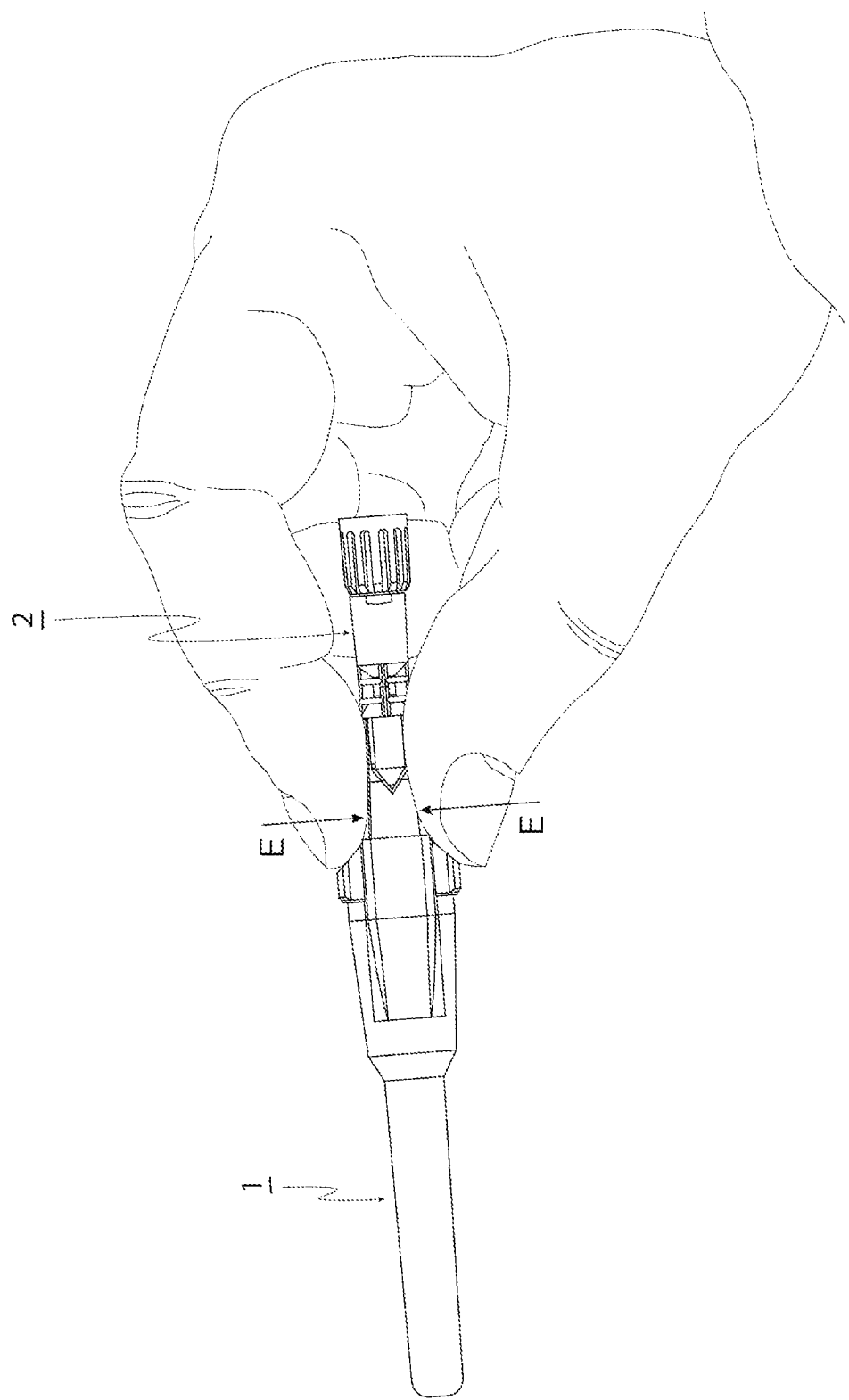
FIG. 8 is a perspective view illustrating a use method of the medical needle assembly according to the first embodiment of the present invention.

According to these configurations, it is possible to convert the force (force in the arrow E direction in FIG. 8 and FIG. 10(a)) of pressing the proximal end portion 6c of the protector 1 into the force (refer to arrow F in FIG. 10(a) and FIG. 11(a)) of causing, via the inclined surfaces 6h and 6i, the protector 1 to move forward. As described above, the notches 6f and 6g are formed on the front side and the rear side of the proximal end portion 6c of the protector 1. Consequently, it is easy to place the fingertips of the thumb and the index finger or the middle finger along the pressing parts (inclined surfaces 6h and 6i) of the proximal end portion 6c of the protector 1, which improves operability during detaching of the protector 1.

As illustrated in FIG. 2, the inclined angle of each of the inclined surfaces 6h and 6i relative to the center axis of the protector 1 is preferably in the range of 45°±10°. According to this preferable configuration, it is possible to efficiently convert the force of pressing the proximal end portion 6c of the protector 1 into the force of causing, via the inclined surfaces 6h and 6i, the protector 1 to move forward.

In other words, the distance (thickness of the inclined surfaces 6h and 6i) in the arrow E direction by which the inclined surfaces 6h and 6i are pressed by fingers is substantially equal to the distance by which the protector 1 is moved forward. Consequently, it is possible to cause the protector 1 to move forward by an appropriate distance with an appropriate pressing force, and the pressing area (length of each of the inclined surfaces 6h and 6i in the axial direction) thus has an appropriate size, which improves operability. If the inclined angle of each of the inclined surfaces 6h and 6i is less than 35°, a force for pressing is not easily converted into a force in a forward moving direction, and the protector 1 is thus not detached unless strongly pressed, which decreases operability. If the inclined angle of each of the inclined surfaces 6h and 6i is more than 55°, the pressing area (length of each of the inclined surfaces 6h and 6i in the axial direction) is smaller, and pressing is thus difficult, which decreases operability.

(Use Method of Medical Needle Assembly)

A use method of the medical needle assembly according to the first embodiment of the present invention will be described with reference to FIGS. 1 to 11.

To detach the protector 1 from the medical needle 2, first, the fingertips of the thumb and the index finger or the middle finger are respectively placed along the inclined surfaces 6h and 6i at the edges of the notches 6f and 6g of the proximal end portion 6c of the protector 1, as illustrated in FIG. 1, FIG. 2, FIG. 8, FIG. 10(a), and FIG. 11(a). Next, in this state, a force is applied in the arrow E direction in FIG. 8 and FIG. 10(a) toward the center of the protector 1 in the radial direction such that the inclined surfaces 6h and 6i are gripped. In other words, when the protector 1 is detached with the right hand, the inclined surface 6h of the notch 6f is pressed with the pad of the thumb, and the inclined surface 6i of the notch 6g is pressed with the pad of the index finger or the pad of the middle finger. When the protector 1 is detached with the left hand, the inclined surface 6h of the notch 6f is pressed with the pad of the index finger or the pad of the middle finger, and the inclined surface 6i of the notch 6g is pressed with the pad of the thumb. The force of pressing the inclined surfaces 6h and 6i in the arrow E direction is thereby converted into the force (force of causing the protector 1 to move forward in the arrow F direction in FIG. 10(a) and FIG. 11(a)) of pressing out, via the inclined surfaces 6h and 6i, the protector 1 in the axial direction. As a result, as illustrated in FIG. 6, the fitted state between the fitting portions 4g and 4h and the fitted portions 6d and 6e is released, and, as illustrated in FIG. 10(b) and FIG. 11(b), the protector 1 can be detached from the medical needle 2.

Note that the forward movement distance (length of each of the inclined surfaces 6h and 6i in the axial direction) indicated in FIG. 6(b) is longer than the fitting distance (length of each of the fitted portions 6d and 6e in the axial direction) indicated in FIG. 6(b). Consequently, the fitted state between the fitting portions 4g and 4h and the fitted portions 6d and 6e is released, and the protector 1 can be detached from the medical needle 2.

Figure 9:
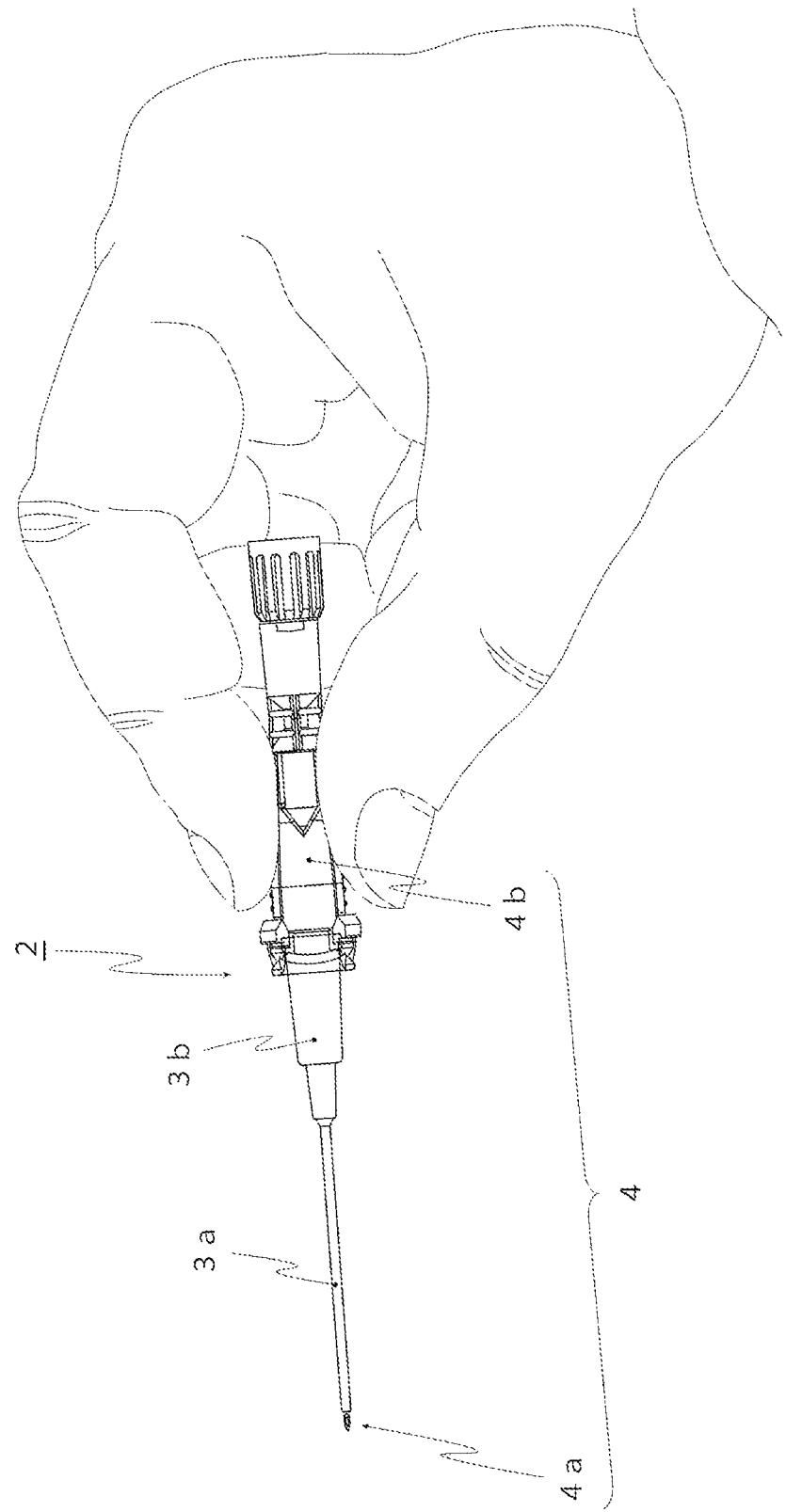
FIG. 9 is a perspective view illustrating a state immediately after the protector is detached from the medical needle in the first embodiment of the present invention.

In the state in which the protector 1 is thus detached, a part in the vicinity of the distal end portion of the hub 4b of the medical needle 2 is in a state of being gripped by the fingertips of the thumb and the index finger or the middle finger, as illustrated in FIG. 9. Thus, re-gripping of the medical needle 2 is not required to perform puncture, and it is possible to immediately enter a puncture stand-by state. In other words, it is possible to perform puncture without changing a holding position. In addition, it is possible to improve precision in puncture with respect to a target site by holding a portion closer to the needle tip when gripping the hub 4b of the medical needle 2 to thereby reduce the effect of hand shake.

Puncture, fluid infusion, or the like is performed as follows. A target site is determined while a blood vessel to be punctured is stretched and straightened with one hand (left hand), and disinfection of an area around the target site is performed using the other hand (right hand). In a state in which the blood vessel is confirmed with the one hand (left hand), the inclined surfaces 6h and 6i are pressed in the arrow E direction by the fingertip (finger pad) of the thumb of the other hand (right hand) and the fingertip (finger pad) of the index finger or the middle finger of the other hand (right hand), and the protector 1 is thereby detached. Next, the target site is punctured in a state in which the metal inner needle 4a is inserted through the catheter 3a as illustrated in FIG. 5 and FIG. 9, the hub 4b is gripped by the fingertips of the thumb and the index finger or the middle finger of the right hand after backflow blood is confirmed through the backflow-blood confirmation portion 4e, and only the inner needle 4 is extracted. Next, a connector of a fluid infusion tube is connected to the catheter hub 3b, and fluid infusion or the like is performed through the catheter 3a indwelling in the blood vessel.

As described above, the use of the medical needle assembly according to the present embodiment enables disinfection of a site to be punctured, detaching of the protector 1, puncture, and needle extraction to be performed using the other hand (right hand), without re-gripping of the medical needle assembly, while a blood vessel to be punctured is confirmed with the one hand (left hand). Thus, operability during a period between detaching of the protector 1 and puncture is improved.

An example in which the medical needle is a venous indwelling needle to be used for fluid infusion (drip infusion) or the like is presented above to describe the present embodiment. The present invention is, however, not necessarily limited to such a configuration. The medical needle to which the protector is attached may be another type of medical needles, for example, a dialysis indwelling needle for use in dialysis or a non-indwelling injection needle.

In addition, forming the notches in the pressing parts of the proximal end portion of the protector according to the present invention is optional provided that the pressing parts have inclined surfaces.

Moreover, the shape of each notch of the pressing parts of the proximal end portion of the protector is not limited to the arc shape. For example, the notches may have a V-shape.

Figure 13:
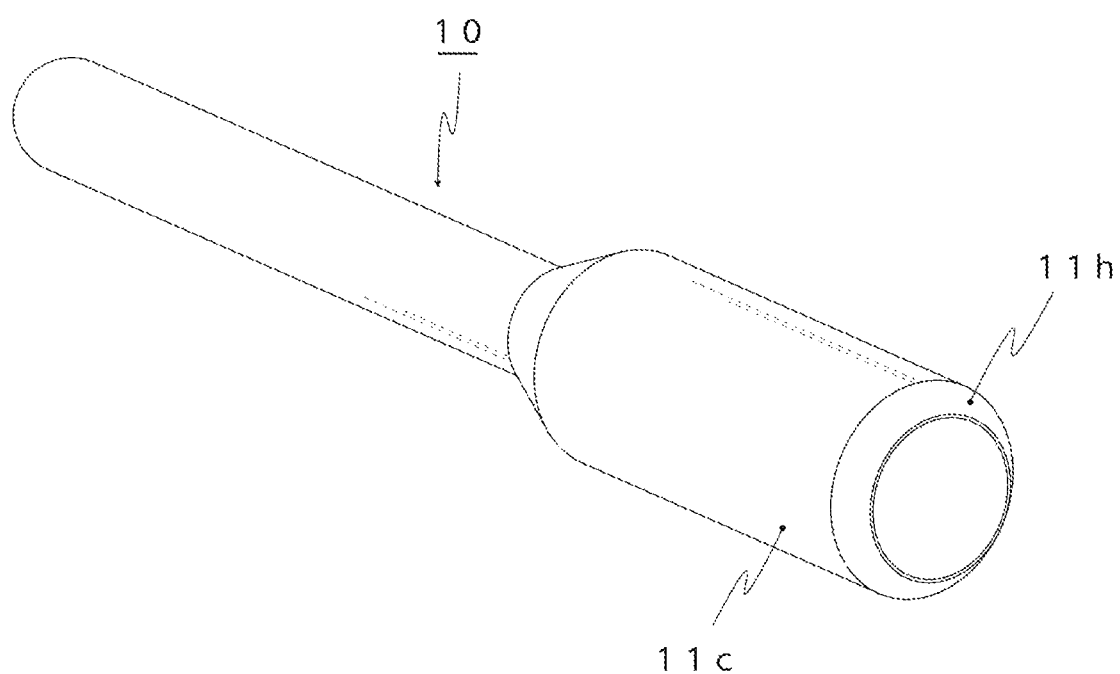
FIG. 13 is a simplified perspective view illustrating another configuration of the protector according to the present invention.

In addition, an inclined surface according to the present invention may be formed at at least one location in the proximal end portion of the protector. For example, as illustrated in FIG. 12, an inclined surface 9h may be formed on only the front side of a proximal end portion 9c of a protector 8. Moreover, as illustrated in FIG. 13, an inclined surface 11h may be formed around the whole circumference of a proximal end portion 11c of a protector 10.

In addition, an example in which the inclined angle of each of the inclined surfaces 6h and 6i relative to the center axis of the protector 1 is in the range of 45°±10° is presented above to describe the present embodiment. The present invention is, however, not necessarily limited to such a configuration. The inclined angle of each of the inclined surfaces 6h and 6i relative to the center axis of the protector 1 is preferably in the range of 45°±5°, and it is possible to more efficiently convert the force of pressing the proximal end portion 6c of the protector 1 into the force of causing, via the inclined surfaces 6h and 6i, the protector 1 to move forward. The inclined angle of each of the inclined surfaces relative to the center axis of the protector may be in the range between 0° and 90° provided that the forward movement distance of the protector is larger than the fitting distance of the protector and the medical needle when the inclined surfaces are gripped by the fingertips of the thumb and the index finger or the middle finger. As the inclined angle increases or decreases from 45°, force conversion efficiency decreases. Ease of detaching the protector 1 is, however, adjustable by, for example, decreasing the strength of fitting between the hub 4b and the protector 1 or improving the force conversion efficiency by using a low-frictional-resistance material for the protector 1.

In addition, an example in which the fitting portions 4g and 4h are formed on the outer circumferential surface of the distal end portion of the hub 4b of the medical needle 2 and in which the fitted portions 6d and 6e each having the recessed shape substantially identical to the shape of the distal end of each of the fitting portions 4g and 4h are formed on the inner circumferential surface of the proximal end portion 6c of the protector 1 is presented above to describe the present embodiment. The present invention is, however, not necessarily limited to such a configuration. For example, a fitting portion having a projecting shape may be formed on the inner circumferential surface of the proximal end portion of the protector, and a fitted portion having a recessed shape substantially identical to the shape of the distal end of the fitting portion may be formed on the outer circumferential surface of the distal end portion of the hub of the medical needle.

In addition, an example in which the pressing parts of the proximal end portion of the protector are positioned in the vicinity of the distal end portion of the hub in the state in which the protector 1 is attached to the medical needle 2 is presented above to describe the present embodiment. The present invention is, however, not necessarily limited to such a configuration. In the state in which the protector 1 is attached to the medical needle 2, the pressing parts of the proximal end portion of the protector may be slightly away from the distal end portion of the hub.

The pressing parts (inclined surfaces 6h and 6i) of the protector 1 and a portion (anti-slip ribs 4c and 4d) of the hub 4b of the medical needle 2 each have a shape so as to be simultaneously grippable by the fingertips. Consequently, it is possible to detach the protector 1 smoothly without causing the medical needle 2 to move together with the protector 1 moving forward when the protector 1 is detached from the medical needle 2 by a one-hand operation.

Second Embodiment (Configurations of Protector and Medical Needle Assembly)

Configurations of a protector and a medical needle assembly according to a second embodiment of the present invention will be described with reference to FIG. 14 and FIG. 15.

Comparing the present embodiment with the aforementioned first embodiment, the present embodiment differs from the first embodiment in terms of only that wings are provided on a medical needle and that slits through which the wings are to be passed are provided in the protector. Other configurations of the present embodiment are identical to those of the aforementioned first embodiment. Members or portions identical to those in the aforementioned first embodiment are thus given identical reference signs, and detailed description thereof is omitted.

Figure 14:
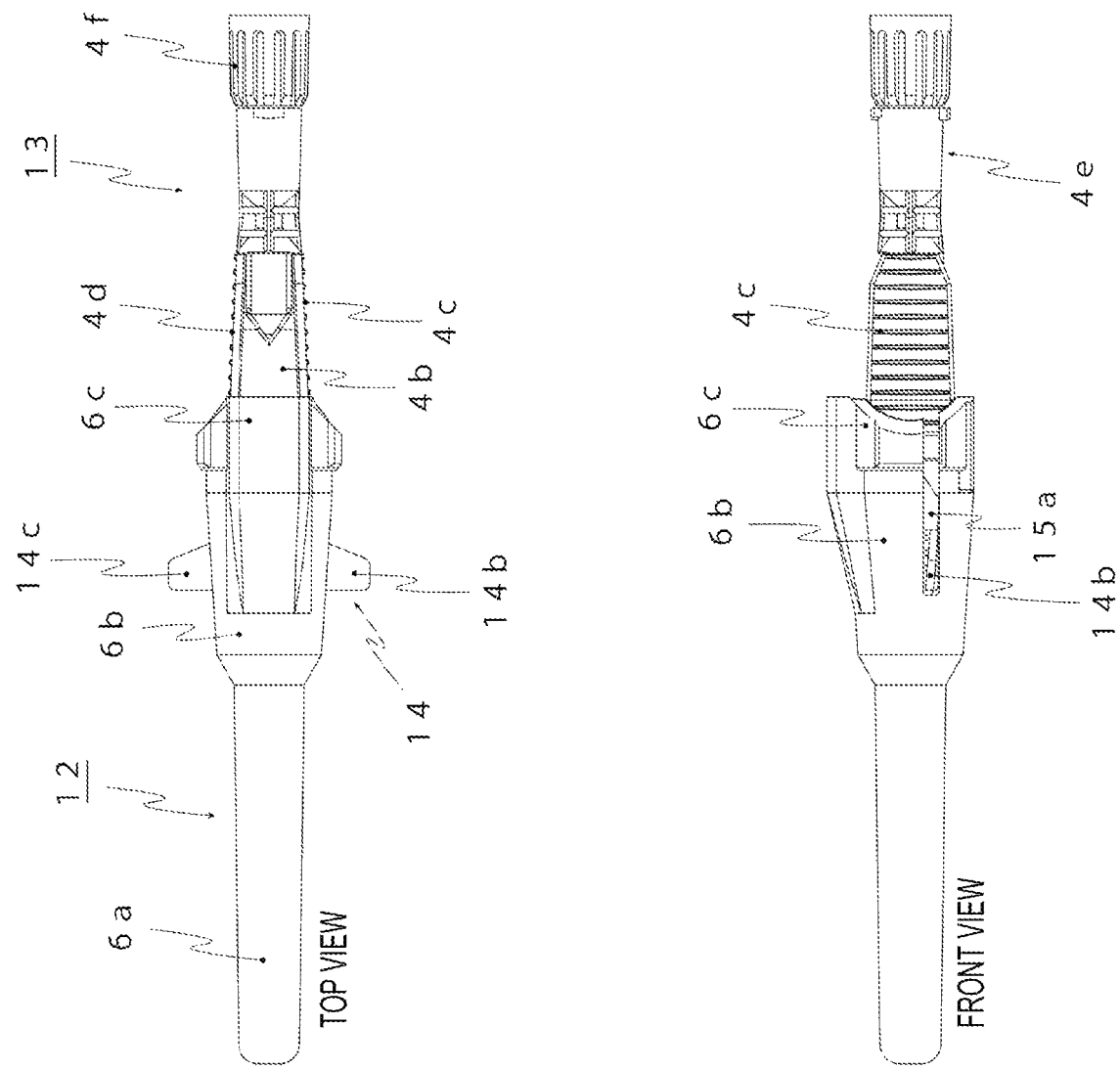
FIG. 14 is a top view and a front view illustrating a configuration of a medical needle assembly according to a second embodiment of the present invention.
Figure 15:
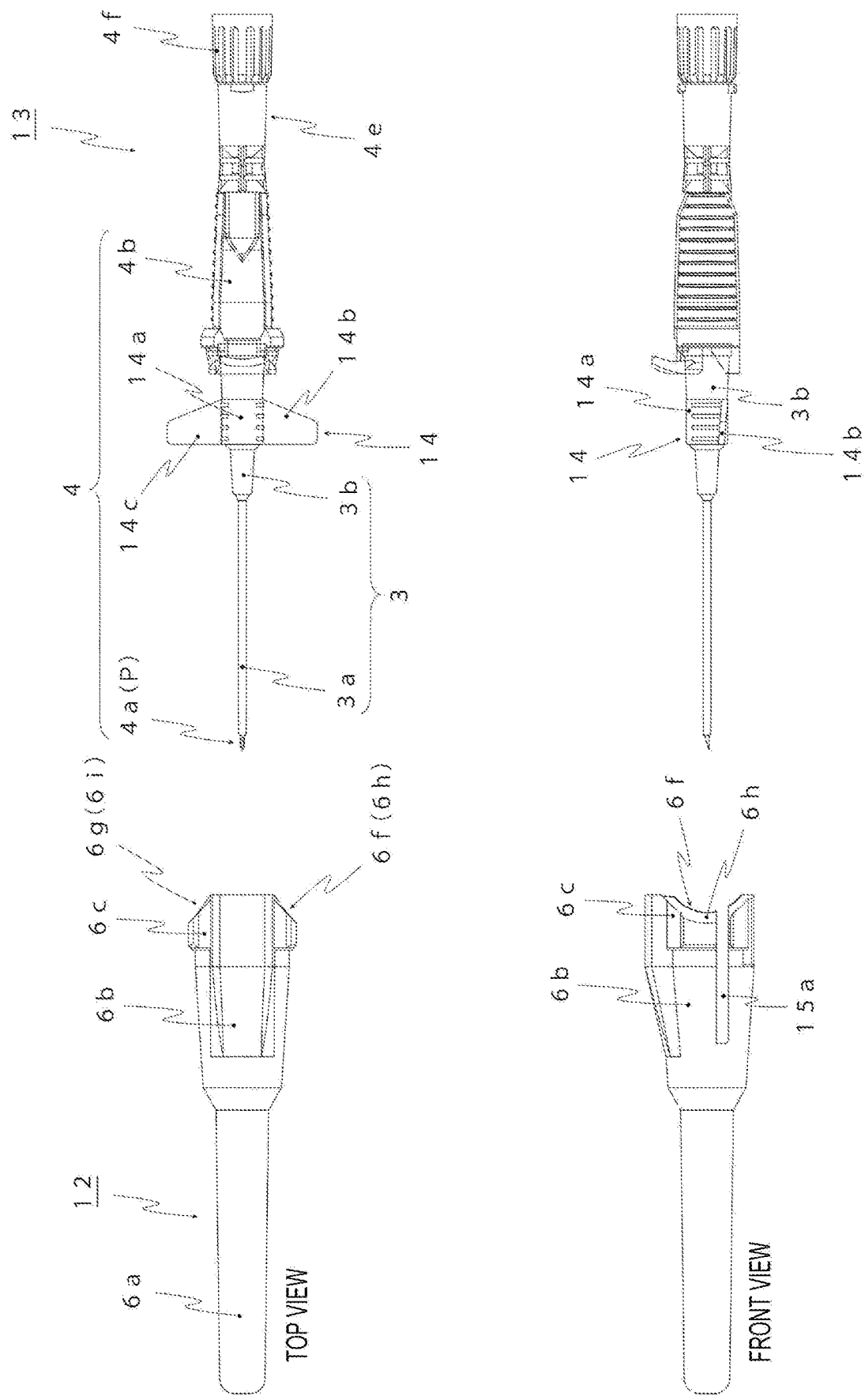
FIG. 15 is an exploded plan view and an exploded front view illustrating the configuration of the medical needle assembly according to the second embodiment of the present invention.

A medical needle 13, illustrated in FIG. 14 and FIG. 15, is a venous indwelling needle and includes the outer needle 3 and the inner needle 4. The outer needle 3 includes a wing 14. The wing 14 includes a shaft portion 14a having a hollow shape and a pair of wing portions 14b and 14c. The shaft portion 14a is externally fitted and fixed to an outer circumference portion of the catheter hub 3b. The wing portions 14b and 14c are each formed to have a plate shape so as to be elastically deformable and are each provided so as to extend leftward and rightward, respectively, from a lower portion of the shaft portion 14a. The wing portions 14b and 14c are fixed to a patient (an arm, a hand, or the like of the patient) with an adhesive tape after puncture is performed and the inner needle 4 is extracted. Consequently, it is possible to firmly fix the outer needle 3 to the patient.

A protector 12 has a left-right pair of slits 15a and 15b (right slit 15b is not illustrated). The slits 15a and 15b are each U-shaped and extend from the edges of the notches 6f and 6g to an intermediate portion of the second protector body portion 6b in the axial direction. The slits 15a and 15b are slits through which the wing portions 14b and 14c are passed when the medical needle 13 and the protector 12 are fitted to each other. The wing portions 14b and 14c are restricted inside the slits 15a and 15b in terms of movement thereof in the vertical direction and the circumferential direction. Consequently, it is possible to suppress wobbling of a protector 16.

The positional relationships between the notches 6f and 6g, the slits 15a and 15b, and the wing portions 14b and 14c are dimensioned such that the rear ends of the wing portions 14b and 14c do not overlap the notches 6f and 6g when the medical needle 13 and the protector 12 are fitted to each other. The wing portions 14b and 14c do not interfere with detaching of the protector 12.

Also in the medical needle assembly according to the present embodiment, when the proximal end portion 6c of the protector 12 is pressed toward the center of the protector 12 in the radial direction in a state in which the protector 12 is attached to the medical needle 13 as illustrated in FIG. 14, the protector 12 is moved forward in the axial direction. The fitted state is thereby released as illustrated in FIG. 15, and the protector 12 is detached from the medical needle 13.

(Use Method of Medical Needle Assembly)

Next, a use method of the medical needle assembly according to the second embodiment of the present invention will be described. As illustrated in FIG. 14, in the state in which the protector 12 is attached to the medical needle 13, the wing portion 14b is passed through the slit 15a and the wing portion 14c is passed through the slit 15b.

Operation to detach the protector 12 from the medical needle 13 is identical to that in the aforementioned first embodiment. When the protector 12 is moved forward, the wing portions 14b and 14c are extracted (from the state illustrated in FIG. 14 to the state illustrated in FIG. 15) from rear open ends of the slits 15a and 15b.

Puncture, fluid infusion, or the like is performed as follows. That is, a target site is punctured in a state in which the metal inner needle 4a is inserted through the catheter 3a as illustrated in FIG. 15, the hub 4b is gripped by the fingertips of the thumb and the index finger or the middle finger of the right hand after backflow blood is confirmed through the backflow-blood confirmation portion 4e, and only the inner needle 4 is extracted. Next, the pair of wing portions 14b and 14c is fixed to a patient (an arm, a hand, or the like of the patient) with an adhesive tape to thereby firmly fix the outer needle 3 to the patient. Next, a connector of a fluid infusion tube is connected to the catheter hub 3b, and fluid infusion or the like is performed through the catheter 3a indwelling in a blood vessel.

The slits 15a and 15b according to the present embodiment are each formed such that the wing portions 14b and 14c are passed through the slits 15a and 15b in the state in which the protector 12 is attached; however, the present invention is not limited to such a configuration. The present invention is also applicable to a medical needle in which the catheter hub 3b is provided, as is a so-called Y-shaped needle, with side tubes (branch port). In this case, the slits 15a and 15b are dimensioned such that the wing portions 14b and 14c and the side tubes (not illustrated) are passed through the slits 15a and 15b in the state in which the protector 12 is attached. When the Y-shaped needle includes no wing portion, the slits 15a and 15b are dimensioned such that the side tubes (not illustrated) are passed through the slits 15a and 15b in the state in which the protector 12 is attached.

Third Embodiment (Configurations of Protector and Medical Needle Assembly)

Configurations of a protector and a medical needle assembly according to a third embodiment of the present invention will be described with reference to FIG. 16 and FIG. 17.

Comparing the present embodiment with the aforementioned second embodiment, the present embodiment differs from the second embodiment in terms of only the shape of the slit portions through which the wings are passed. Other configurations thereof are identical to those in the aforementioned second embodiment. Members or portions identical to those in the aforementioned second embodiment are thus given identical reference signs, and detailed description thereof is omitted.

Figure 17:
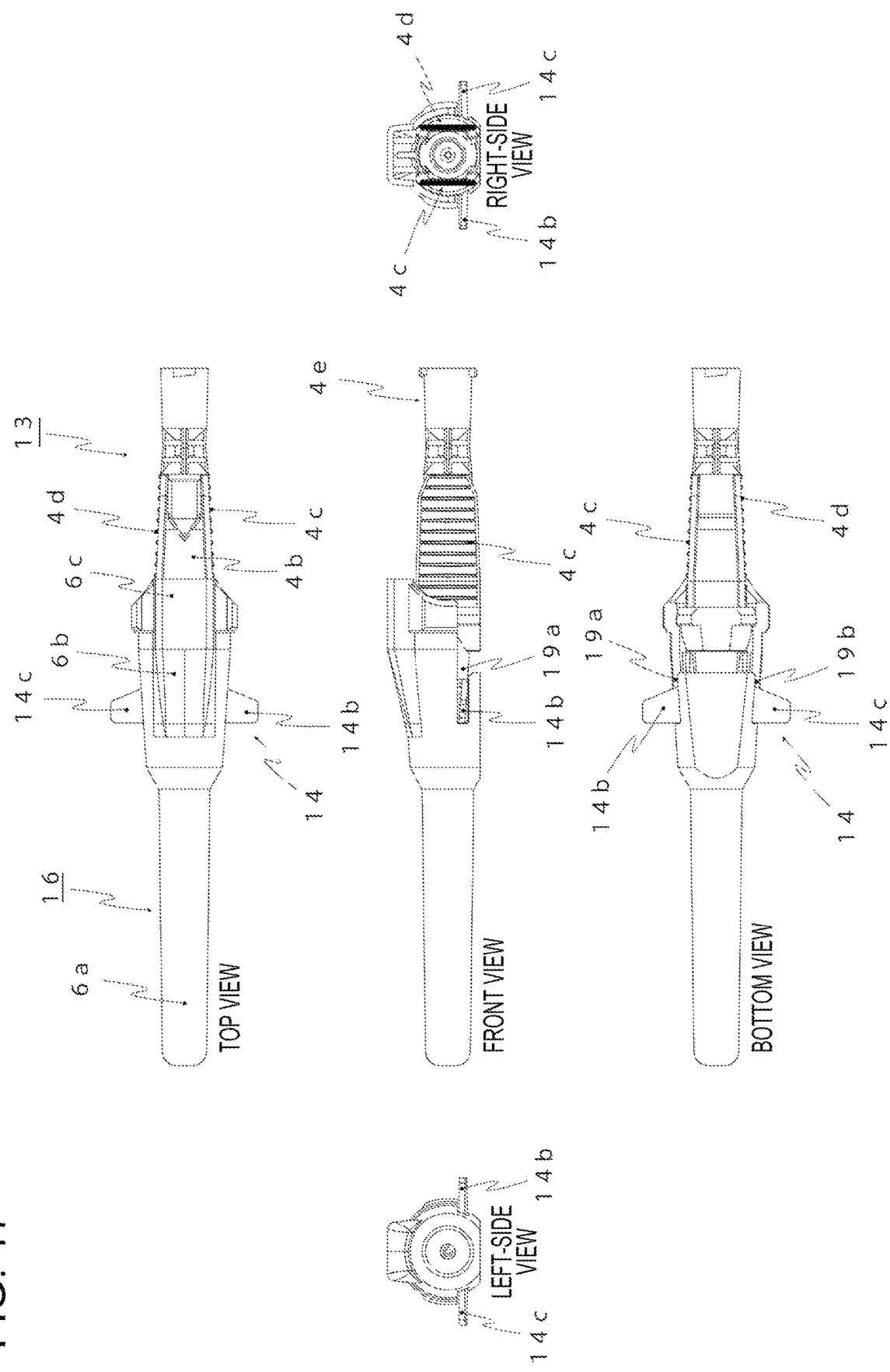
FIG. 17 is a six-view drawing (the rear view, which appears symmetrically with the front view, is omitted, and an air plug is omitted) illustrating a configuration of a medical needle assembly according to the third embodiment of the present invention.

The medical needle 13 illustrated in FIG. 17 is a venous indwelling needle and includes the outer needle 3 and the inner needle 4 (refer to FIG. 15). As illustrated in FIG. 15 and FIG. 17, the outer needle 3 includes the wing 14. The wing 14 includes the shaft portion 14a and the wing portions 14b and 14c.

Figure 16:
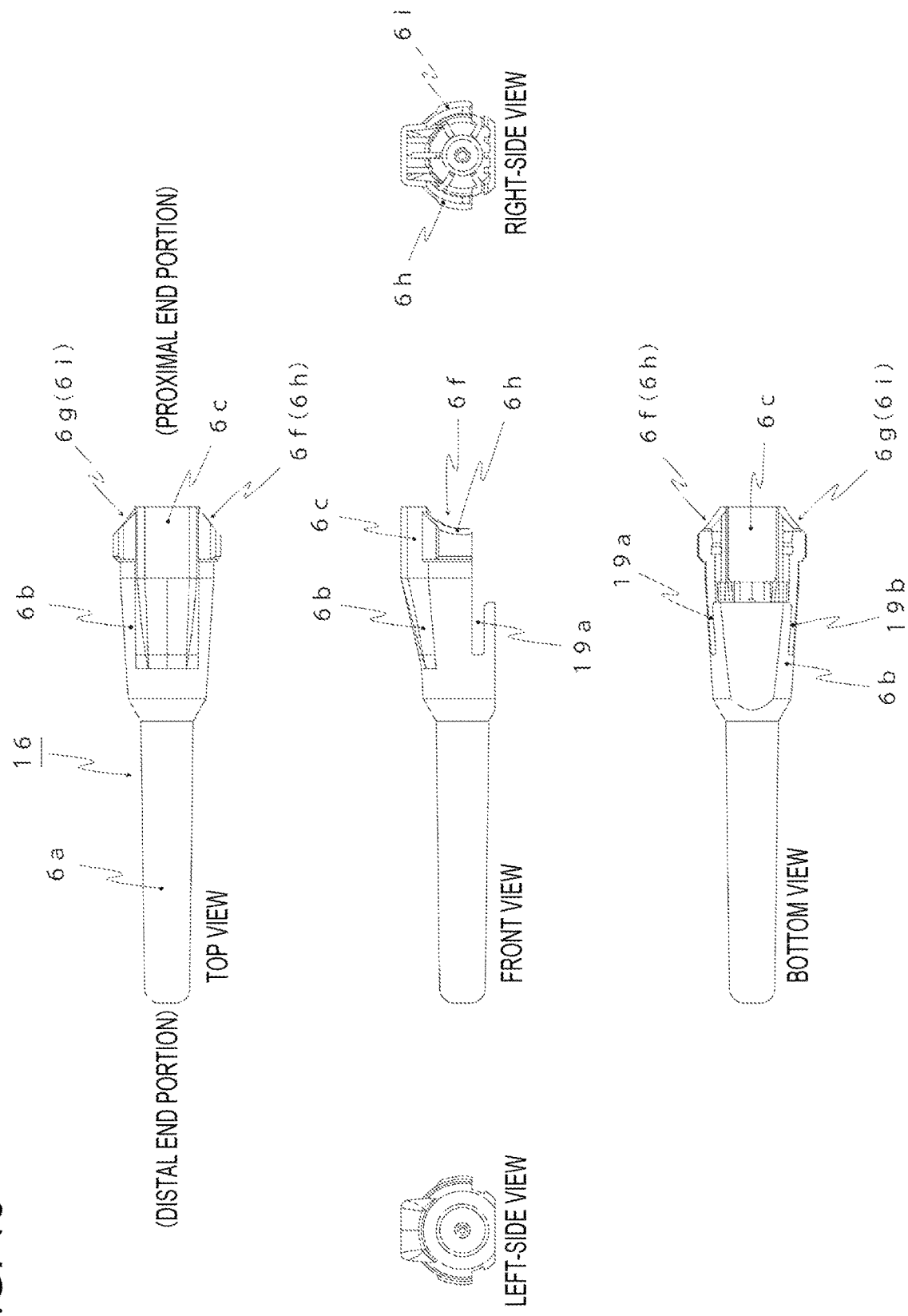
FIG. 16 is a six-view drawing (the rear view, which appears symmetrically with the front view, is omitted) illustrating a configuration of a protector according to a third embodiment of the present invention.

As illustrated in FIG. 16 and FIG. 17, the protector 16 has a left-right pair of slits 19a and 19b. Unlike the protector 12 in the aforementioned second embodiment, a portion of the proximal end portion 6c below the slits 19a and 19b is cut out in the protector 16 according to the present embodiment. In addition, a portion (for example, half the axial-direction length of each of the slits 19a and 19b) of the second protector body portion 6b below the slits 19a and 19b is cut out.

According to such a configuration, it is possible to reduce the quantity of materials of the protector 16 compared with the aforementioned first and second embodiments, which enables a reduction in manufacturing costs and a reduction in product weight. In addition, a portion of the second protector body portion 6b below the slits 19a and 19b is retained. The wing portions 14b and 14c are thus restricted inside the slits 19a and 19b in terms of movement in the vertical direction and the circumferential direction. Consequently, it is possible to suppress wobbling of the protector 16.

Also in the medical needle assembly according to the present embodiment, when the proximal end portion 6c of the protector 16 is pressed toward the center of the protector 16 in the radial direction in a state in which the protector 16 is attached to the medical needle 13 as illustrated in FIG. 17, the protector 16 is moved forward in the axial direction. The fitted state is thereby released, and the protector 16 is detached from the medical needle 13.

(Use Method of Medical Needle Assembly)

Next, a use method of the medical needle assembly according to the third embodiment of the present invention will be described. As illustrated in FIG. 17, in the state in which the protector 16 is attached to the medical needle 13, the wing portion 14b is passed through the slit 19a and the wing portion 14c is passed through the slit 19b.

Operation to detach the protector 16 from the medical needle 13 is identical to that in the aforementioned first embodiment. When the protector 16 is moved forward, the left-right pair of the wing portions 14b and 14c on the medical needle 13 is extracted from rear open ends of the left-right pair of slits 19a and 19b formed in the protector 16.

Puncture, fluid infusion, or the like is performed in a manner similar to that in the aforementioned second embodiment.

REFERENCE SIGNS LIST 1, 8, 10, 12, 16 protector
2, 13 medical needle
3 outer needle
3a catheter
3b catheter hub
4 inner needle
4a metal inner needle
4b hub
4c, 4d anti-slip rib
4e backflow-blood confirmation portion
4f air plug
4g, 4h fitting portion
6a first protector body portion
6b second protector body portion
6c, 9c, 11c proximal end portion
6d, 6e fitted portion
6f, 6g notch
6h, 6i, 9h, 11h inclined surface
14 wing
14a shaft portion
14b, 14c wing portion
15a, 15b, 19a, 19b slit
P needle tip

The invention claimed is:

1. A protector to be detachably fitted and attached to a medical needle, the protector comprising:

an inclined surface provided at a proximal end portion of the protector so as to be externally exposed in a state in which the protector is attached to the medical needle, the inclined surface inclining outwardly in a radial direction of the protector from the proximal end portion toward a distal end portion of the protector, wherein, the inclined surface is a pressing part of the proximal end portion and configured for a finger pressing, and wherein, the inclined surface of the protector is configured to, when the inclined surface of the protector is pressed toward a center of the protector in the radial direction, move forward such that a fitted state of the protector is released and the protector is detached from the medical needle.

2. The protector according to claim 1, wherein an inclined angle of the inclined surface relative to a center axis of the protector is in a range of 45°±10°.

3. The protector according to claim 2, wherein the pressing part of the proximal end portion of the protector is notched.

4. The protector according to claim 3, further comprising a slit through which a wing and/or a side tube of the medical needle is passed.

5. The protector according to claim 2, further comprising a slit through which a wing and/or a side tube of the medical needle is passed.

6. The protector according to claim 1, wherein the pressing part of the proximal end portion of the protector is notched.

7. The protector according to claim 6, further comprising a slit through which a wing and/or a side tube of the medical needle is passed.

8. The protector according to claim 1, further comprising a slit through which a wing and/or a side tube of the medical needle is passed.

9. A medical needle assembly comprising:
   a medical needle that includes a needle body, a hub to which a proximal end portion of the needle body is fixed, and a fitting portion; and
   the protector according to claim 1, the protector including a fitted portion to be fitted to the fitting portion and being detachably attached to the medical needle.

10. The medical needle assembly according to claim 9, wherein the pressing part of the proximal end portion of the protector is positioned in a vicinity of a distal end portion of the hub in a state in which the protector is attached to the medical needle.

* * * * *